United States Patent [19]

Curro et al.

[11] Patent Number: 4,695,422
[45] Date of Patent: * Sep. 22, 1987

[54] PRODUCTION OF FORMED MATERIAL BY SOLID-STATE FORMATION WITH A HIGH-PRESSURE LIQUID STREAM

[75] Inventors: John J. Curro, Cincinnati; Alan J. Trusty, Bethel; George M. Vernon, West Chester, all of Ohio

[73] Assignee: The Procter & Gamble Company, Cincinnati, Ohio

[ * ] Notice: The portion of the term of this patent subsequent to Sep. 1, 2003 has been disclaimed.

[21] Appl. No.: 580,911

[22] Filed: Feb. 16, 1984

[51] Int. Cl.$^4$ .................... B29C 59/06; B29C 69/02
[52] U.S. Cl. .................... 264/504; 264/570; 264/154; 264/280; 264/299; 264/331.11; 264/DIG. 62; 264/DIG. 70; 425/290; 425/326.1; 425/385; 425/387.1; 425/DIG. 37; 425/DIG. 119
[58] Field of Search ............... 264/504, 570, 280, 154, 264/156, DIG. 62, DIG. 70, 299, 331.11; 521/50; 425/290, 326.1, 385, 387.1, DIG. 37, DIG. 119

[56] References Cited

U.S. PATENT DOCUMENTS

| | | | |
|---|---|---|---|
| Re. 23,910 | 12/1954 | Smith et al. | 18/19 |
| 2,123,552 | 7/1938 | Helwig | 18/56 |
| 2,776,451 | 1/1957 | Chavannes | 18/10 |
| 2,776,452 | 1/1957 | Chavannes | 18/10 |
| 2,862,251 | 12/1958 | Kalwaites | 264/119 |
| 2,905,969 | 9/1959 | Gilbert et al. | 18/19 |
| 3,038,198 | 6/1962 | Schaar | 18/1 |
| 3,054,148 | 9/1962 | Zimmerli | 18/56 |
| 3,084,389 | 4/1963 | Doyle | 18/19 |
| 3,605,191 | 9/1971 | Kaspar | 18/15 |
| 3,685,930 | 8/1972 | Davis et al. | 425/71 |
| 3,709,647 | 1/1973 | Barnhart | 425/224 |
| 3,862,282 | 1/1975 | Watson | 264/DIG. 70 |
| 3,929,135 | 12/1975 | Thompson | 128/287 |
| 3,947,174 | 3/1976 | Hureau et al. | 425/72 |
| 3,966,383 | 6/1976 | Bussey, Jr. et al. | 425/388 |
| 3,989,867 | 11/1976 | Sisson | 428/132 |
| 4,151,240 | 4/1979 | Lucas et al. | 264/504 |
| 4,155,693 | 5/1979 | Raley | 425/363 |
| 4,226,828 | 10/1980 | Hall | 264/555 |
| 4,259,286 | 3/1981 | Louis et al. | 264/555 |
| 4,262,049 | 4/1981 | Kaspar | 428/131 |
| 4,280,978 | 7/1981 | Dannheim et al. | 264/156 |
| 4,303,609 | 12/1981 | Hureau et al. | 264/504 |
| 4,317,792 | 3/1982 | Raley et al. | 264/504 |
| 4,327,730 | 5/1982 | Sorensen | 128/287 |
| 4,342,314 | 8/1982 | Radel et al. | 128/287 |
| 4,395,215 | 7/1983 | Bishop | 425/290 |
| 4,609,518 | 9/1986 | Curro et al. | 264/504 |

FOREIGN PATENT DOCUMENTS 0059506 9/1982 European Pat. Off. .

Primary Examiner—Joseph L. Schofer
Assistant Examiner—F. M. Teskin
Attorney, Agent, or Firm—E. Kelly Linman; Milton B. Graff, IV; John V. Golman

[57] ABSTRACT

The present invention provides for a process for transforming a substantially continuous web of substantially planar, deformable material having an indefinite length, a first surface, and a second surface into a formed material. The material has a transformation temperature range. The process comprises the following steps:
(a) The web of material is provided on a forming structure with the first surface of the web of material proximate a forming surface of the forming structure. The forming surface moves in a direction of the length of the web of material and carries the web of material in that direction.
(b) A liquid stream is applied to the second surface of the web of material. The liquid stream has sufficient force and mass flux to cause the web of material to be deformed toward the forming surface, such that the material acquires a substantial three-dimensional conformation.
(c) The temperature of the web of material is controlled such that it remains below the transformation temperature range of the material throughout the process.

33 Claims, 12 Drawing Figures

PRODUCTION OF FORMED MATERIAL BY SOLID-STATE FORMATION WITH A HIGH-PRESSURE LIQUID STREAM

TECHNICAL FIELD

The present invention relates to webs of formed materials, especially polymeric film, exhibiting three-dimensional characteristics, and process and apparatus for producing them. The present invention relates particularly to the production of webs of debossed and perforated materials comprising polymeric film where the film is in a solid state throughout the process.

BACKGROUND OF THE INVENTION

Processes for embossing and for debossing and perforating heat-softened thermoplastic film are known. As used herein, a web of material is a thin, flat, substantially planar web of material of definite, preferably substantially uniform, width and indefinite length. A web of embossed film or other material is such a web of such material in which numerous protuberances have been formed to provide it with a substantial third dimensional structure perpendicular to the plane of the material. A web of debossed and perforated film or other material has protuberances which provide it a third dimensional structure perpendicular to the plane of the material in which many or all of the protuberances have holes. The protuberances of webs of embossed and of debossed and perforated materials may be of a wide variety of sizes and shapes or may all be identical. Collectively such webs of embossed and/or debossed and perforated materials are referred to herein as webs of formed materials; the protuberances of such webs of formed films provide the webs with a three-dimensional bulk conformation.

In prior art processes for producing a web of formed film, a web of heat-softened film is provided on a patterned, perforated outer surface (referred to herein as a forming surface) of a structure such as an endless belt or a drum cylindrical surface. A vacuum beneath the forming surface pulls the heat-softened film into conformity with the forming surface. Alternatively, a positive pressure may be used to force the heat-softened film against the forming surface. Whether the web of film is simply embossed or is debossed and perforated will depend on the size of the holes in the forming surface, the softness and thickness of the film being formed, and the fluid pressure differential across the film.

Processes for producing webs of embossed thermoplastic film are disclosed in U.S. Pat. Nos. Re 23,910 issued to Smith & Smith on Dec. 12, 1954; 2,776,451 and 2,776,452 both issued to Chavannes on Jan. 8, 1957; and 2,905,969 issued to Gilbert & Prendergast on Sept. 29, 1959. Processes for the production of webs of debossed and perforated thermoplastic films are disclosed in U.S. Pat. Nos. 3,038,198 issued to Shaar on June 12, 1962; 3,054,148 issued to Zimmerli on Sept. 18, 1962; 4,151,240 issued to Lucas & Van Coney on Apr. 24, 1979; 4,155,693 issued to Raley on May 22, 1979; 4,226,828 issued to Hall on Oct. 7, 1980; 4,259,286 issued to Lewis, Sorensen & Ballard on Mar. 31, 1981; 4,280,978 issued to Dannheim & McNaboe on July 28, 1981; 4,317,792 issued to Raley & Adams on Mar. 2, 1982; 4,342,314 issued to Radel & Thompson on Aug. 3, 1982; and 4,395,215 issued to Bishop on July 26, 1983. A process for the production of perforated seamless tubular film is disclosed in U.S. Pat. No. 4,303,609 issued to Hureau, Hureau & Gaillard on Dec. 1, 1981.

The processes disclosed in the references cited above require that the thermoplastic film be heat-softened in order to achieve the desired embossing or debossing and perforation of the film. This can be achieved as disclosed in many of the above references by heating an existing web of film to a temperature above its melt temperature range such that it is in a molten state and will readily flow and attain a new configuration. Alternatively, the molten film may be achieved by feeding a web of film direcly from a film extruder onto the forming surface. Such a process is disclosed in U.S. Pat. No. 3,685,930 issued to Davis & Elliot on Aug. 22, 1972, where a web of thermoplastic film is extruded directly onto the outer surface of an endless belt and a vacuum is pulled beneath the belt to make the molten web of film assume the configuration of the outer belt surface. Similarly, U.S. Pat. No. 3,709,647 isseud to Barnhart on Jan. 9, 1973, discloses a web of molten thermoplastic film extruded directly onto the outer cylindrical surface of a vacuum forming drum.

It is known to shape molten thermoplastic sheet material by the use of a fluid pressure forcing the sheet against a mold; such processes are disclosed in U.S. Pat. Nos. 2,123,552 issued to Helwig on July 12, 1938; and 3,084,389 issued to Doyle on Apr. 9, 1963.

The production of a foraminous material by deposition of liquid latex on the surface of a rotating cylinder is disclosed in U.S. Pat. Nos. 3,605,191 and 4,262,049 both issued to Kasper on Sept. 20, 1971, and Apr. 14, 1981, respectively. Holes in the latex film may be achieved by rupturing with high pressure water jets.

When webs of embossed or debossed and perforated thermoplastic film are produced on a patterned surface by the above prior art processes, it is generally necessary to cool the film below its melt temperature range to set its three-dimensional structure prior to removing the web of formed film from the forming surface. This makes the web of formed film much less susceptible to distortion of its bulk conformation.

This need to cool and set a web of formed film prior to its removal from the forming surface is often a rate limiting step in the production of such formed film. A substantial amount of cooling of webs of formed film can occur by heat transfer from the film to the forming surface. In Davis & Elliott, such heat transfer is enhanced by cooling the endless belt after stripping the web of formed film from the belt and before a web of molten film is again applied to the belt. In Barnhart, a cooling medium is used inside the drum to cool the forming surface.

Cooling can also be assisted by contacting the outer film surface with an external cooling medium while the web of formed film is on the forming surface. For webs of debossed and perforated film, cooling of the formed film is usually assisted by drawing air through the perforations with vacuum prior to removing the web of formed film from the forming surface; such a cooling process is disclosed, for example, in Lucas & Van Coney. Chavannes '452 discloses contacting a web of embossed film with a wet belt to cool the film. Gilbert & Prendergast discloses use of a water spray to cool a web of embossed film on the forming surface of an embossing drum. Doyle discloses cooling vacuum formed molten thermoplastic sheet with a water mist.

A disadvantage of making webs of formed film by these prior art processes is the need to have the film within or above its melt temperature range in order to form the film. This limits the range of desired properties that can be engineered into the formed film since all previous thermo-mechanical history of the film is erased. Also, the rapid cooling of the formed film necessary for retention of the desired bulk conformation of the film produces a very limited set of molecular morphologies and, hence, limited range of physical properties in the resultant formed film.

SUMMARY OF THE INVENTION

It is an object of the present invention to provide a process for producing webs of formed materials at high speed.

It is a further object of the present invention to provide such a process where the material is not heated to within or above its transformation temperature range so that desired physical properties of the starting material are retained in the formed material.

It is a still further object of the present invention to provide such a process which is capable of forming a wide variety of materials.

It is also an object of the present invention to provide apparatus for the high-speed production of web of formed materials.

It is also an object of the present invention to provide debossed and perforated materials which exhibit a surface roughness on the land areas between the protuberances and on a portion of the inner sidewalls of the protuberances.

It is a further object of the present invention to provide debossed and perforated materials having perforated protuberances of substantially different size adjacent one another.

It is a still further object of the present invention to provide debossed and perforated materials having protuberances of a wide variety of shapes.

The present invention provides a process for transforming a substantially continuous web of substantially planar, deformable material having an indefinite length, a first surface, and a second surface into a formed material. The material has a transformation temperature range. The process comprises the steps of:
  (a) providing the web of material on a forming structure with the first surface of the web of material proximate a forming surface of the forming structure, the forming surface moving in a direction of the length of the web of material and carrying the web of material in that direction;
  (b) applying a liquid stream to the second surface of the web of material, the liquid stream having sufficient force and mass flux to cause the web of material to be deformed toward the forming surface, such that the material acquires a substantial three-dimensional conformation; and
  (c) controlling temperature of the web of material such that it remains below the transformation temperature range of the material throughout the process.

DETAILED DESCRIPTION OF THE INVENTION

Figure 1:
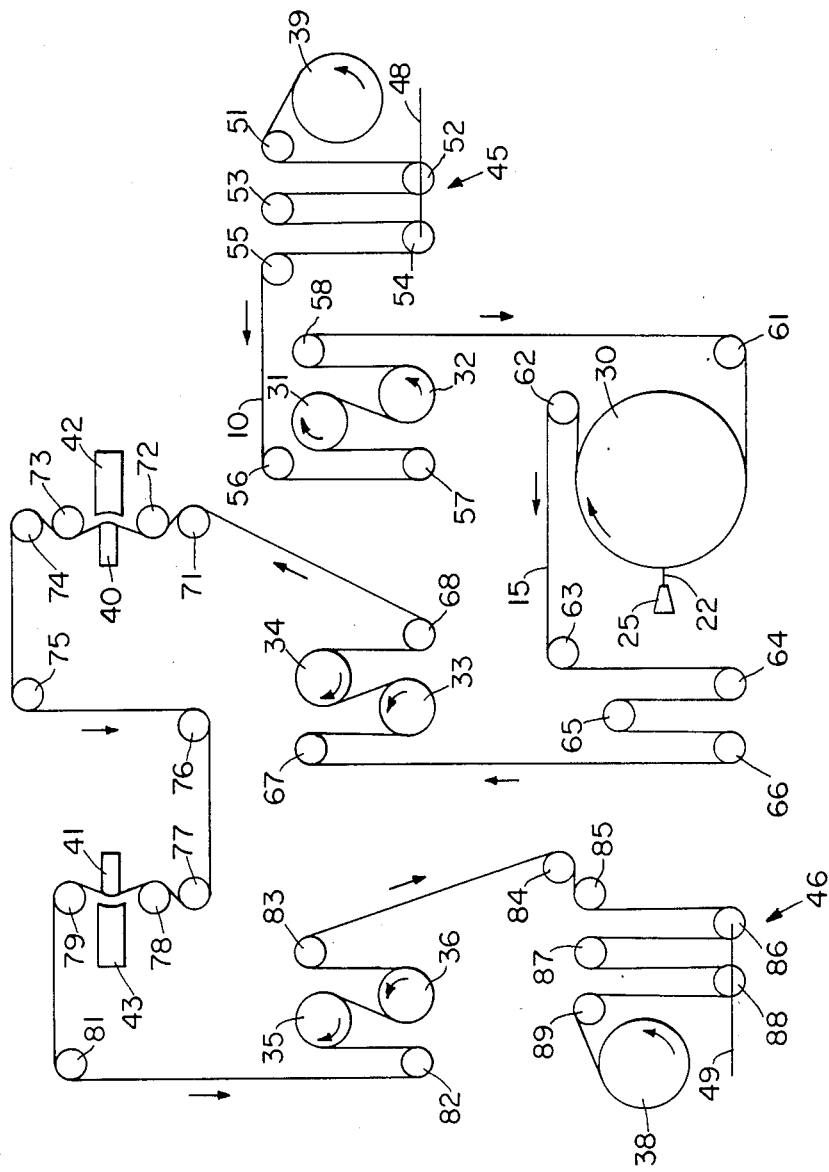
FIG. 1 is a schematic flow diagram of a process of the present invention for producing webs of formed material.

Processes of the present invention are used to produce webs of embossed and/or debossed and perforated material from webs of substantially planar, deformable material. With the processes of the present invention, both embossing and debossing and perforating can be achieved on the same web of material. Also, perforated protuberances of the formed material may have greatly varying shapes and sizes, even within the same formed material.

Deformable material as used herein describes a material which, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials. The processes of the present invention are preferably used to form materials comprising a polymeric film; such materials include polymeric films themselves and laminates comprising polymeric films and other materials.

Deformable materials utilized in processes of the present invention have a transformation temperature range where changes in the solid-state molecular structure of the material occur, such as a change in crystalline structure or a change from solid to molten state. As a consequence, above the transformation temperature range, certain physical properties of the material are substantially altered. For a thermoplastic film, the transformation temperature range is the melt temperature range of the film, above which the film is in a molten state and loses substantially all previous thermo-mechanical history.

Webs of deformable material which are embossed and have bulk conformation, especially webs of embossed polymeric film, are produced by processes of the present invention. Such embossed materials are used where the material is desired to have a design provided by the embossments, or where a textured material is desired.

Webs of deformable materials which are debossed and perforated and have bulk conformation, especially webs of debossed and perforated polymeric films, are produced by preferred processes of the present invention. Such debossed and perforated films can be engineered to provide a variety of bulk conformations which will provide certain liquid handling characteristics.

A debossed and perforated film may be used, for example, as a top sheet in an absorptive structure having tapered capillaries. Such structures, including disposable diapers, incontinent pads, bandages, and the like, are disclosed in U.S. Pat. No. 3,929,135 issued to Thompson on Dec. 30, 1975. Another potential use for such debossed and perforated film is as a breatheable backsheet for disposable absorbent device such as those disclosed in U.S. Pat. No. 3,989,867 issued to Sisson on Nov. 2, 1976.

Webs of material prior to forming by the processes of the present invention are substantially "planar". For purposes of clarity, the term "planar", when utilized herein to describe such webs of material, refers to the overall condition of the web of material when viewed on a macroscopic scale. In this context, planar webs of material may include webs of material having fine-scale surface texture (surface roughness) on one or both sides, or may be fibrous or woven. By surface roughness, it is meant that third dimensional structure of the substantially planar material is substantially less than the third dimensional structure (bulk conformation) imparted to the material by the processes of the present invention. For example, a thermoplastic film having a matte finish or even a fine embossed surface pattern, can be debossed and perforated by processes of the present invention; the debossed and perforated conformation is on a large scale in the direction perpendicular to the substantially planar material compared to the structure of the matte finish or fine embossed pattern. A desirable attribute of processes of the present invention is that such a matte finish or fine embossed pattern of a film can be substantially retained on the surface of the debossed and perforated film.

The primary prior art processes for producing webs of embossed and of debossed and perforated thermoplastic film, as disclosed in several of the references cited hereinbefore, entails vacuum forming of a web of molten thermoplastic film. An exemplary vacuum film forming process is disclosed in *Lucas & Van Coney* cited hereinbefore. In such a process, the cylindrical surface of a drum has a patterned, perforated outer surface (forming surface) having a surface configuration desired to be imparted to a web of film. The forming surface has holes through which a fluid can pass. A vacuum beneath the forming surface causes the molten thermoplastic film to be urged against and conform to the forming surface.

The processes of the present invention can be advantageously used to form webs of embossed and/or debossed and perforated thermoplastic film. The processes of the present invention can also be used for embossing and/or debossing and perforating webs of other materials which comprise polymers, especially materials which comprise polymeric film. For example, laminates of polymeric film and metal foil, polymeric film and woven or nonwoven fabric, and polymeric film and paper can be embossed and/or debossed and perforated according to the processes of the present invention. Such other materials often cannot be embossed or debossed and perforated by the prior art processes because the materials cannot withstand the high temperature (above the melt temperature range of a thermoplastic polymer) to which the material must be raised in order to achieve the formation of the material, or because the pressure differential available with a vacuum forming apparatus is not sufficient to force the material to conform to the forming surface.

The webs of formed materials produced according to the processes of the present invention preferably comprise thermoplastic polymers having characteristic rheological properties which depend on their composition and temperature. Below their glass transition temperature, such thermoplastic polymers are quite hard and stiff and often brittle. Below this glass transition temperature, the molecules are in rigid, fixed positions.

Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. The processes of the present invention are preferably utilized to form materials comprising thermoplastic polymer, especially thermoplastic film, which is within this viscoelastic temperature range.

Above the melt temperature range, thermoplastic polymers are in a molten state and large-scale, cooperative molecular motions become possible. The molecular arrangement of a molten thermoplastic polymer is random when the polymer is at equilibrium. Thus any non-random molecular arrangement in a thermoplastic polymer will be lost if its temperature is raised above and maintained above its melt temperature range for a sufficient time. The prior art thermoplastic film-forming processes disclosed hereinabove form the film while it is above its melt temperature range in a molten state.

Webs of materials which can be used to produce webs of formed materials according to the processes of the present invention must be deformable, preferably to the extent of that they can substantially conform to the forming surface on which they are formed. This requires a certain minimum amount of ductility in the web of material to be formed. Ductility, as used herein, is the amount of permanent, unrecoverable, plastic strain which occurs when a material is deformed, prior to failure (breakage or separation) of the material. In order to be formed, materials formed in processes of the present invention preferably have a minimum ductility of at least about 10%, more preferably at least about 100%, more preferably still at least about 200%.

FIG. 1 is a schematic flow diagram of an exemplary process of the present invention for producing webs of debossed and perforated materials. A substantially continuous web of substantially planar material is fed to the process by any conventional means such as from large feed roll 39. The web of material is preferably web of polymeric film, more preferably a web of thermoplastic film 10 which may be a pure thermoplastic substance, a mixture of thermoplastic substances, or a mixture of thermoplastic substances with other components. Preferred thermoplastic materials used to produce webs of formed film in the present invention include materials normally cast as films such as polyolefins, nylons, polyesters, and the like. Especially preferred thermoplastic materials used in the present invention are polyethylenes, low density polyethylenes, linear low density polyethylenes, polypropylenes and copolymers and blends containing substantial fractions of these materials.

Web of film 10 is pulled from storage roll 39 by driven S-wrap rolls 31 and 32. Web of film 10 is pulled through tension controlled device 45 around idler rolls 51, 52, 53, 54 and 55. Idler rolls 52 and 54 are attached to pivoted bar 48. The tension of web of film 10 is controlled by the force placed on web of film 10 through pivot arm 48 and rolls 52 and 54 of tension control device 45. Web of film 10 feeds from tension control device 45 around idler rolls 56 and 57 to driven S-wrap rolls 31 and 32.

Web of film 10 is pulled around idler rolls 58 and 61 by driven forming drum 30. Roll 58 is also a tension measuring roll Model No. PB-O, available commercially from Cleveland Machine Controls, Inc., Cleveland, Ohio. Web of film 10 is debossed and perforated on forming drum 30 by the action of liquid stream 22 from spray system 25, thus producing web of formed film 15. The film forming process will be described in greater detail hereinafter. Idler roll 61 is preferably a hollow roll with holes in its cylindrical surface; this helps avoid slippage of web of film 10 on roll 61 due to liquid getting between web of film 10 and the roll surface.

Web of formed film 15 is pulled from forming roll 30 by the action of driven vacuum S-wrap rolls 33 and 34. Web of formed film 15 is pulled around idler roll 62, also preferably a hollow roll with holes in its cylindrical surface, and idler rolls 63, 64, 65, 66, and 67 which provide numerous changes of direction of the film and allow liquid to drain from and be thrown from web of formed film 15. Roll 67 is a tension measuring roll. Driven S-wrap rolls 33 and 34 are preferably hollow rolls with holes in their cylindrical surfaces with a vacuum pulled on the interior of the rolls. The vacuum in these rolls provides a dual purpose. It holds the somewhat wet, slippery web of formed film 15 more securely to the roll surfaces thus avoiding slippage of web of film 15. It also removes some liquid from web of film 15.

Web of formed film 15 is pulled from vacuum S-wrap rolls 33 and 34 by driven S-wrap rolls 35 and 36. Web of formed film 15 is pulled around idler rolls 68, 71, and 72 and past ultrasonic drying horn 40. Ultrasonic drying horn 40 uses ultrasonic energy to vibrate web of formed film 15 thus atomizing residual droplets of liquid on web of formed film 15 which are drawn into manifold 42 by vacuum. Web of formed film 15 is then pulled around idler rolls 73, 74, 75, 76, 77, and 78 and past ultrasonic drying horn 41 and vacuum manifold 43 to dry the other surface of web of formed film 15. Ultrasonic drying horns 40 and 41 in conjunction with vacuum manifolds 42 and 43 thus provide drying of web of formed film 15 without excessive heating of the film. If further drying of web of formed film 15 is necessary, web 15 is preferably passed through a low temperature air drying tunnel. Web of formed film 15 is pulled over idler rolls 79, 81, and 82 to driven S-wrap rolls 35 and 36. Roll 82 is a tension measuring roll.

Web of formed film 15 is pulled from S-wrap rolls 35 and 36 by driven take-up roll 38. Web of formed film 15 is pulled around idler rolls 83, 84, 85, 86, 87, 88, and 89 and through tension controlling device 46 to take-up roll 38. The tension on web of formed film 15 is controlled by the force provided by pivot bar 49 and its attached idler rolls 86 and 88 on web of formed film 15.

The tracking and tension of web of film 10 and web of formed film 15 in the exemplary process shown in FIG. 1 is preferably aided by a slight draw (stretch) of the film between the driven rolls. For example, forming drum 30 is driven such that its surface speed is slightly faster than that of driven S-wrap rolls 31 and 32; this helps retain good tension and tracking of web of film 10 between them. Similarly, vacuum S-wrap rolls 33 and 34 are driven such that their surface speed is slightly faster than that of forming drum 30, and so on through the process. The preferred amount of draw (stretch) between sequential driven rolls will depend on the material being formed, the distance between the driven rolls, the extent and geometry of perforations (if any) in the material, and the temperature of the material in that portion of the process. For webs of low density polyethylene formed by the exemplary process shown in FIG. 1, draws of from about 1% to about 15% between sequential driven rolls (a pair of S-wrap rolls is considered as if it were one driven roll) have typically been used.

Figure 2:
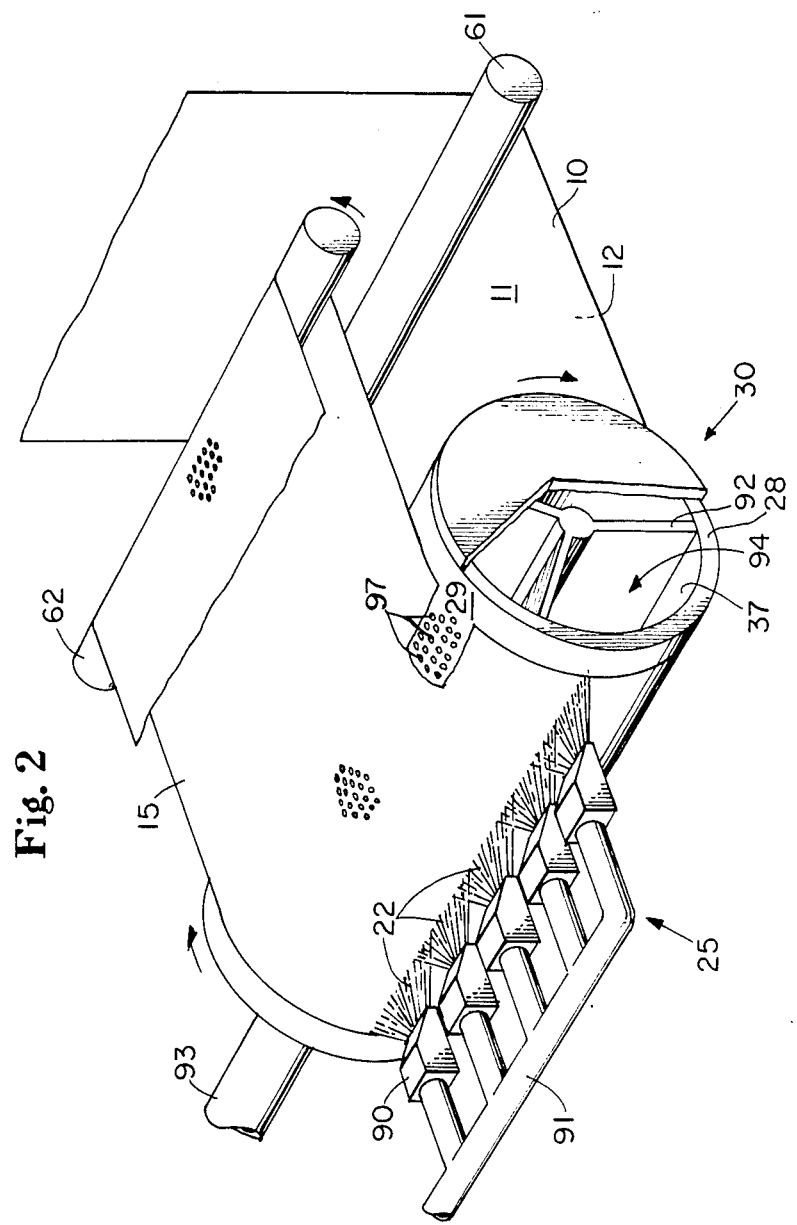
FIG. 2 is a simplified schematic perspective illustration of preferred apparatus for forming a web of material.
Figure 3:
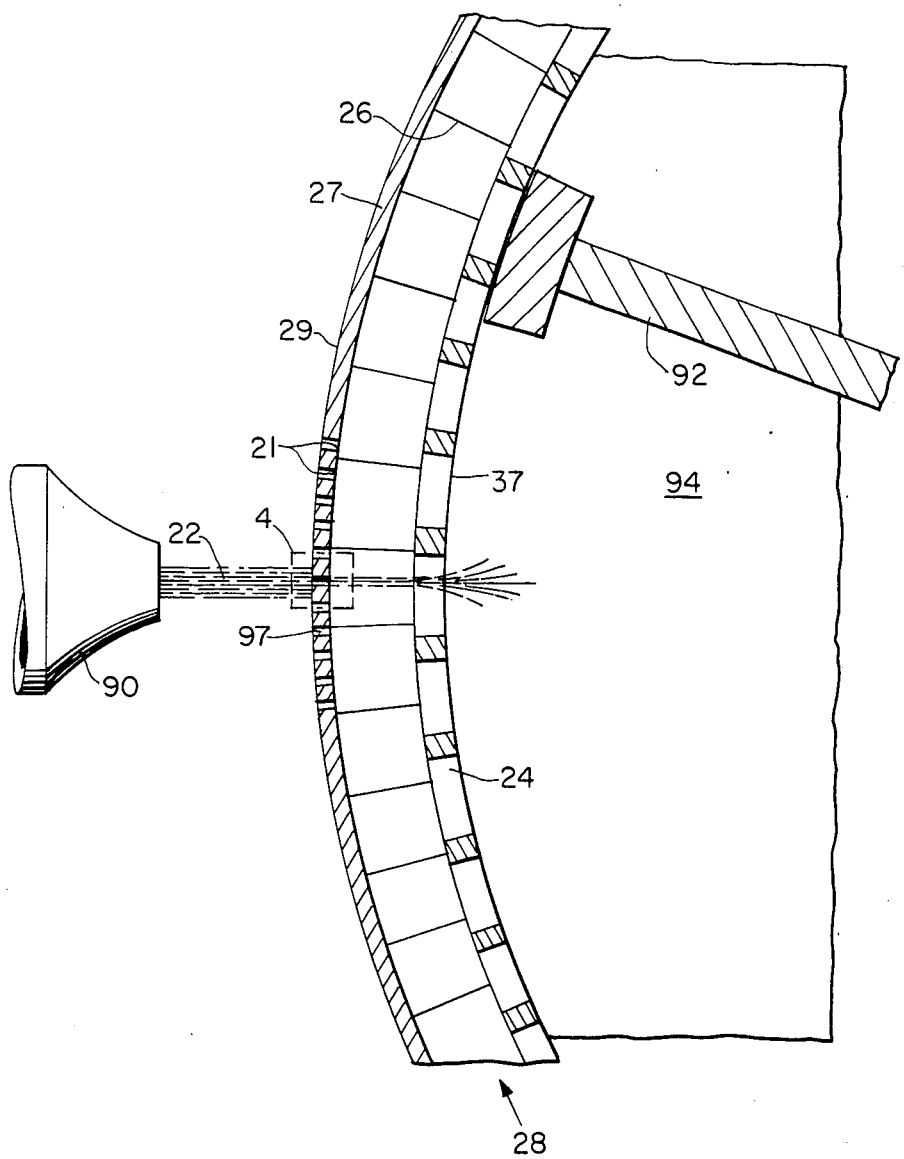
FIG. 3 is a simplified schematic cut-away end view of a portion of the apparatus shown in FIG. 2.
Figure 4:
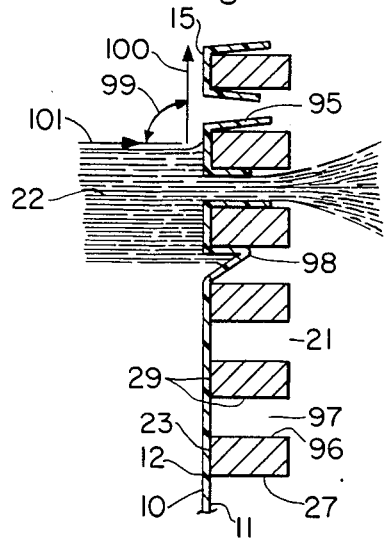
FIG. 4 is an enlarged view of Area 4 of FIG. 3.

The present invention provides an apparatus for debossing and perforating a substantially continuous web of substantially planar material having an indefinite length. FIGS. 2, 3 and 4 are simplified schematic perspective views of an exemplary apparatus and depict the operation of forming drum 30 and spary system 25. The apparatus has tubular forming structure 28 having patterned forming surface 29 and opposed surface 37. Web of film 10 has first surface 11 and second surface 12. Web of film 10 is provided on forming structure 28 with first surface 11 of web of film 10 proximate patterned forming surface 29 of forming structure 28. For apparatus on which debossed and perforated materials are to be produced, forming structure 28 preferably comprises depressions 97 which have sidewalls 96 and end in holes 21. Forming structure 28 is open from holes 21 in forming surface 29 to opposed surface 37. The apparatus has means for moving forming surface 29 in a direction of the length of the web of material being formed (web of film 10). The apparatus has means for applying liquid stream 22 to second surface 12 of web of film 10 with sufficient force and mass flux to cause perforations to be created in web of film 10. At least a portion of liquid stream 22 flows through the perforations in web of film 10, through holes 21 in forming surface 29, and through forming structure 28. Liquid stream 22 has sufficient force and mass flux to cause web of film 10 to be extended into depressions 97 and to cause first surface 11 of web of film 10 to be deformed toward sidewalls 96 of depressions 97, such that perforated protuberances 95 are formed in web of film 10. Web of formed film 15 is thus produced. The apparatus has means for controlling temperature of web of film 10 such that the material remains below its transformation temperature range (melt temperature range).

Examples of forming structures and forming surfaces which can be used on forming drum 30 to produce webs of formed materials according to the processes of the present invention, and supporting structures for such forming structures are disclosed in *Lucas & Van Coney; Radel & Thompson;* Bishop; commonly assigned allowed patent application of William I. Mullane entitled METHOD AND APPARATUS FOR UNIFORMLY DEBOSSING AND APERTURING A RESILIENT PLASTIC WEB, Ser. No. 230488, filed Feb. 2, 1981, allowed on June 24, 1983 and issued on Apr. 10, 1984 as U.S. Pat. No. 4,441,952; and commonly assigned patent application of William I. Mullane entitled UNIFORMLY DEBOSSING AND APERTURING A MOVING PLASTIC WEB USING STATIONARY SUPPORT MEMBER IN FORMING AREA, Ser. No. 542,796 filed on Oct. 17, 1983 and now abandoned; all of which are hereby incorporated by reference.

Exemplary tubular forming structure 28 for producing webs of debossed and perforated materials is shown in FIG. 3 which is a simplified schematic cut-away end view of a portion of the apparatus shown in FIG. 2. Tubular forming structure 28 consists of three concentric tubular elements bonded together: forming screen 27, honeycomb 26, and perforated plate 24. Forming screen 27 has forming surface 29 against which web of film 10 (not shown in FIG. 3) is formed. Forming surface 29 has depressions 97 which have sidewalls 96 and end in holes 21, and land areas 23 surrounding depressions 97. Depressions 97 provide concavities in forming screen 27 where debossed and perforated protuberances are formed in web of film 10. Forming screen 27 is supported by honeycomb 26 which is typically a ¼ inch deep hexagonal honeycomb structure made from stainless steel ribbon about 0.05 mm in thickness bent and brazed to form hexagonal cells about ¼ inch across. The thickness of the cell walls of honeycomb 26 are preferably sufficiently thin such that none of holes 21 are totally blocked by the walls of honeycomb 26. Perforated plate 24 supports honeycomb 26 and is typically made from perforated stainless steel sheet metal about 2 mm in thickness having holes of about 6 mm diameter on centers about 8 mm apart. Opposed surface 37 of forming structure 28 coincides with the inner surface of perforated plate 24. The openings in honeycomb 26 and perforated plate 24 line up sufficiently such that there is no substantially total obstruction to fluid flow from any of holes 21 of forming surface 29 through forming structure 28 to opposed surface 37. Therefore, forming structure 28 is open from holes 21 in forming surface 29 to opposed surface 37.

Where embossed (non-preforated) protuberances are to be formed in web of film 10, forming screen 27 would preferably have concavities which do not end in holes in forming surface 29. The depth of the embossed protuberances which can be formed using processes of the present invention depend on the material being formed, the thickness of the material, the temperature of the forming liquid, etc. If the concavities of forming surface 29 are made too deep, the proturberances will be perforated. For areas where it is desired that there be no embossed or debossed and perforated protuberances in the material being formed, forming surface 29 is maintained substantially flat (without concavities or holes).

Tubular forming structure 28 is driven in a direction of the length of web of film 10, as shown in FIG. 2, and carries web of film 10 in that direction past spray system 25. Liquid stream 22 is applied from spray system 25 to second surface 12 of web of film 10. Liquid stream 22 has sufficient force and mass flux to cause web of film 10 to be deformed toward forming surface 29 and preferably to substantially conform to the image of forming surface 29. Thus, web of film 10 acquires a substantial three-dimensional conformation and is transformed into web of formed film 15.

Spray system 25 may be any means for applying a liquid stream to second surface 12 of web of film 10 with sufficient force and mass flux to deform web of film 10. An exemplary spray system, as shown in FIG. 2, provides a high-pressure liquid (preferably water) spray across the entire width of web of film 10. Water is provided at high pressure through manifold 91 to spray nozzles 90. Spray nozzles 90 are preferably conventional high-pressure spray nozzles which preferably provide liquid stream 22 in a flat, fan-shaped spray having a fan angle of no more than about 60°, more preferably no more than about 30°, as measured in the cross-machine direction. Such narrow spray angles help to insure good film formation and prevent angled protuberances which can be caused by an angled direction of liquid stream 22. Spray nozzles 90 are preferably aligned such that the narrowest dimension of the flat spray is parallel to the machine direction (direction of movement of forming surface 29), and such that the spray from adjacent nozzles overlaps somewhat so that the entire second surface 12 of web of film 10 is contacted by liquid stream 22 as web of film 10 passes by spray system 25. If only a portion of the width of web of film 10 is being formed, only a corresponding portion of forming surface 29 will have a three-dimensional conformation. In such case, spray nozzles 90 can alternatively be set such that liquid stream 22 is applied only to those width portions of web of film 10 to be formed.

The processes of the present invention are preferably carried out utilizing materials comprising thermoplastic polymers, especially thermoplastic films, having viscoelastic properties. Web of formed film 15 will not generally conform precisely to the configuration of forming surface 29. The bulk conformation of web of formed film 15 will depend on the temperature, force and mass flux of liquid stream 22 as well as film properties and the configuration of forming surface 29. At higher temperatures, forces, and mass flux of liquid stream 22, web of formed film 15 will conform closer to forming surface 29. But because preferred web of thermoplastic film 10 has visco-elastic properties throughout the forming process, some "spring-back" of web of formed film 15 generally occurs after it passes liquid stream 22. This visco-elastic behavior of the thermoplastic film being formed makes it possible to achieve variations in the bulk conformation of web of formed film 15 by varying the temperature, force, and mass flux of liquid stream 22.

The processes of the present invention are particularly suitable for producing webs of embossed and/or debossed and perforated deformable materials where it is desirable to retain physical properties engineered into the substantially planar starting web of material. In the manufacture of substantially planar thermoplastic film, certain physical properties such as tensile strength, tear strength, ductility, tensile, modulus, anisotropic features of such properties, surface finish (e.g. matte finish), surface chemistry, pre-embossment, etc., can be engineered into the film through manufacturing techniques which may result, for example, in desired molecular orientations in the film, desired crystalline morphologies, desired surface appearance of the film, desired tactile properties of the film, etc. The temperature of a web of material being formed in a process of the present invention is controlled such that it remains below the transformation temperature range of the material throughout the forming process. Thus, a preferred process of the present invention achieves formation of a web of thermoplastic film at a temperature below its melt temperature range.

The processes of the present invention can produce webs of formed thermoplastic film at a temperature below the melt temperature range of the film due to the large force and mass flux available when using a high-pressure liquid stream to form the film. Prior art processes generally depend on forming webs of film by using the pressure differential achieved by pulling a vacuum beneath the forming surface and having normal atmospheric pressure on the opposed surface of the film. Such pressure differential is thus limited to about one atmosphere and is generally not sufficient to form thermoplastic film which is at a temperature below its melt temperature range. The force and mass of the liquid stream needed to form a web of material will depend on a number of factors including the composition, thickness, and temperature of the material being formed.

The successful forming of web of film 10 depends on liquid stream 22 from nozzles 90 having sufficient force and mass flux to deform web of film 10 toward the configuration of forming surface 29 of forming strucure. 28. The ability of liquid stream 22 to form web of film 10 depends on the pressure of the liquid flowing through nozzles 90 of spray system 25, the mass and distribution of liquid impinging on surface 12 of web of film 10, the distance between nozzles 90 and surface 12 of web of film 10, the temperature of liquid stream 22, and the surface speed of drum 30, as well as the composition, thickness, and temperature of web of film 10.

The processes of the present invention are particularly suitable for producing webs of debossed and perforated thermoplastic film while retaining the film in its solid state throughout the process. Although the scope of the present invention is not limited to a particular mechanism for forming film, it is believed that the mechanism of film formation in solid state differs from that of prior art processes where the film is in a molten state.

When molten film is debossed and perforated by the action of a vacuum beneath a patterned, perforated surface, the molten film is drawn into a depression in the forming surface and the molten film readily and rapidly acquires the image of the forming surface. subsequent to this forming action, the molten film over the hole in the forming surface is extended until it ruptures, thus forming the perforation in the protuberance of the formed film.

Formation of debossed and perforated film in the solid state appears to differ in mechanism from that in the molten state in that the perforation in each protuberance often occurs before the protuberance acquires its finished shape in a depression in the forming surface. This mechanism is shown schematically in FIGS. 4 and 5. Forming screen 27, which is shown in cross section, has forming surface 29 which consists of land areas 23 and sidewalls 96 of depressions 97 which end in holes 21. When liquid stream 22 initially impinges a portion of film over depression 97 and hole 21 in forming surface 29, that portion of film is stretched into depression 97 in a relatively straight-sided V-shape 98, if permitted by the configuration of sidewalls 96 of depression 97. The portion of film is stretched beyond its yield point and subsequently ruptures, usually near the point of the V, thus perforations are created in the film. After perforation, at least a portion of liquid stream 22 flows through the perforations in the film and through holes 21 in forming surface 29. This liquid flow forces the sidewalls of film protuberances 95 toward sidewalls 96 of depression 97 in forming surface 29. The extent to which the film conforms to the configuration of forming surface 29 can be controlled by the mass flux and force of liquid stream 22 on the film. The spring-back tendency of the film in its visco-elastic state depends on the degree of deformation and the time/temperature reciprocal visco-elastic relationship inherent to solid state thermoplastic film. Therefore, such spring-back can be substantially controlled by the force and mass flux, as well as the temperature, of impinging liquid stream 22 on web of film 10.

Regardless of the mechanism for forming perforated protuberances 95 of debossed and perforated film 15, liquid stream 22 must have sufficient force and mass flux to cause first surface 11 of web of film 10 to be deformed toward forming surface 29 and to cause perforations to be created in web of film 10, thus causing web of film 10 to be debossed and perforated. In the formation of embossed films, liquid stream 22 must have sufficient force and mass flux to cause web of film 10 to deform toward the image of forming surface 29. The liquid pressure and flow required to form web of film 10 will vary greatly depending on the properties of the film being formed and the speed of the forming operation.

Web of film 10 is more easily perforated and formed in the configuration of forming surface 29 if liquid steam 22 is heated to a temperature approaching the melt temperature range of the film, but is sufficiently below such melt temperature range in order to insure that web of formed film 15 retains the desired physical properties of web of film 10. For forming of the preferred thermoplastic films disclosed herein with water, anytemperature which maintains the water in a liquid state can be used. Preferred water temperatures are from about 40° C. to about 90° C.; more preferred are from about 65° C. to about 75° C. Preferred water pressures are preferably at least about 350 N/cm$^2$ (500 psig), more preferably from about 700 N/cm$^2$ (1000 psig) to about 1100 N/cm$^2$ (1600 psig) or greater.

Using the processes of the present invention, webs of substantially planar thermoplastic film, such as polyethylenes, low density polyethylenes, linear low density polyethylenes, polypropylenes, and copolymers and blends containing substantial fractions of these materials can be successfully debossed and perforated. For economic reasons, webs of formed film as thin as possible while still retaining sufficient strength are generally desired. Such webs of film preferably have a thickness of no more than about 1.0 mm, more preferably no more than about 0.06 mm, more preferably still the film thickness is from about 0.01 mm to about 0.04 mm. Such webs of film are fed into processes of the present invention at a temperature below the melt temperature range of the film; generally such webs of film are fed at the ambient temperature of the room where the process is being carried out.

For exemplary forming structure 28, the water which flows through the perforations of web of formed film 15 after the film ruptures flows on through forming structure 28 into chamber 94 of forming drum 30. Stationary manifold 92 can be present inside forming drum 30 to provide partitions which define chamber 94 within forming drum 30.

Although it is not necessary in the production of webs of formed film by processes of the present invention, a vacuum may be drawn on chamber 94 for two purposes. Chamber 94 preferably extends from the portion of forming structure 28 where web of film 10 first contacts forming surface 29 of forming structure 28 to somewhat beyond the area of impingement of liquid stream 22 on second surface 12 of web of film 10. A vacuum in chamber 94 provides a means for securely holding web of film 10 against forming surface 29 of forming structure 28 prior to the forming of web 10, so that web of film 10 does not slip on surface 29. Chamber 94 extends beyond the area where liquid stream 22 is debossing and perforating web of film 10 so that most of the liquid from liquid stream 22 flows into chamber 94 either with the aid of vacuum or without. The liquid collected in chamber 94 is discharged through pipe 93. If liquid is able to get between web of formed film 15 and forming surface 29, problems such as slipping, distortion, or tearing of web of formed film 15 can occur. By discharging most of the liquid away from the system through chamber 94 and pipe 93, such problems are generally minimized. If vacuum in chamber 94 is used, it need only be a low level to achieve the desired purposes of holding web of film 10 securely against forming surface 29 and/or drawing liquid away from forming surface 29. Thus any vacuum level in chamber 94 is preferably far below that required to substantially deform web of film 10. A preferred vacuum level in chamber 94 is from 0 to about 250 mm Hg; more preferred is from about 15 to about 50 mm Hg.

The use of a high-pressure liquid stream to produce webs of formed material provides for many alternatives in the products produced. Many of these alternatives are not achievable or are much more difficult to achieve when using the prior art vacuum forming of webs of molten thermoplastic film. FIG. 11 is a perspective fragmentary view of an exemplary debossed and perforated film 150 of the present invention. Film 150 of FIG. 11 can be produced using exemplary forming screen 127 shown in FIG. 10.

Figure 10:
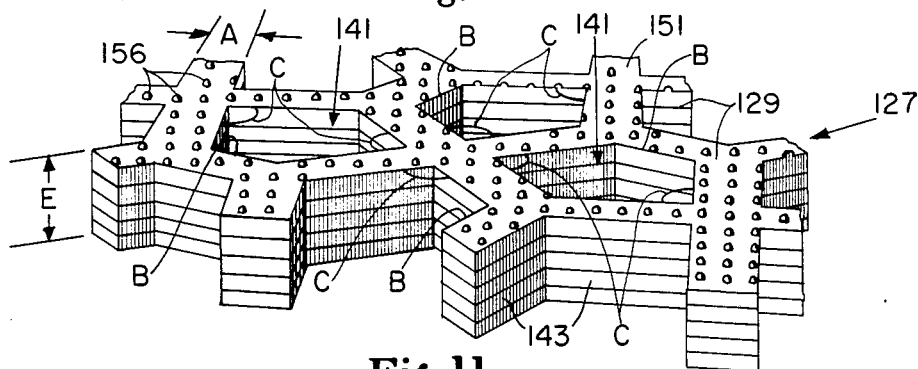
FIG. 10 is a fragmentary enlarged perspective view of an exemplary forming screen used to produce debossed and perforated materials according to the present invention.
Figure 11:
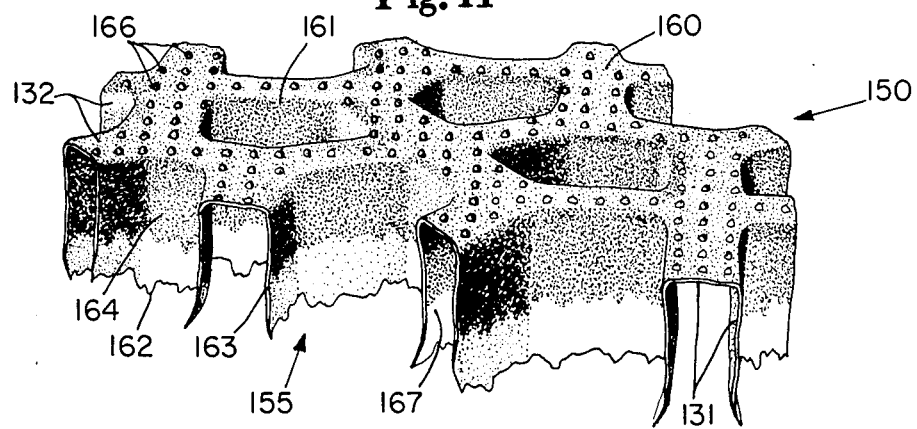
FIG. 11 is a fragmentary enlarged perspective view of an exemplary debossed and perforated film of the present invention.

The pattern and structure of forming screen 127 used to produce web of formed film 150 is shown in FIG. 10. Such a forming screen can be made as disclosed in Radel & Thompson cited hereinbefore. The pattern of forming surface 129 of forming screen 127 consists of a repeated pattern of nested pentagonal depressions 141 with land area 151 between the depressions. Forming surface 129 consists of land area 151 and sidewalls 143 of pentagonal depressions 141 which are substantially perpendicular to land area 151 and extend through forming screen 127, thus forming pentagonal holes in forming surface 129. The open area in forming surface 129 created by these pentagonal holes is about 67% of the projected surface area of forming screen 127. Dimension A across all ribs of land area 151 between parallel sides of adjacent pentagons is about 0.178 mm. Each pentagon has one side B about 0.477 mm long and the other four sides about 0.651 mm long. Each pentagon has two 90° angles C which are never adjacent angles and are always formed by two of the equal length sides of the pentagon. Dimension E which is the thickness of forming screen 127 is about 1.3 mm. Forming screen 127 has an outer diameter of about 129 cm and is made from stainless steel.

Debossed and perforated materials of the present invention comprise a polymeric film having a first surface and a second surface separated by a thickness. Such materials have a land area with an upper surface which defines a plane and comprises a portion of the second surface of the film, and a lower surface which comprises a portion of the first surface of the film. Exemplary debossed and perforated film 150 of FIG. 11 has first surface 131 and second surface 132 separated by a maximum thickness T. It is preferably made from a polymeric film having a substantially uniform thickness T. For formed film 150, a plane is defined by the upper surface of land area 160 of formed film 150. Stating that a plane is defined by the upper surface of land area 160 simply indicates that formed film 150 can be laid out such that land area 160 is substantially flat; it is understood that formed film 150 is flexible and can conform to many non-flat shapes.

Debossed and perforated materials of the present invention comprise perforated protuberances such as perforated protuberances 155 of formed film 150. Each protuberance 155 has a first aperture 161 located in the plane of the upper surface of land area 160, and a second aperture 162 wholly remote from and below said plane. Each protuberance 155 has sidewall 163 which continuously interconnects first aperture 161 and second aperture 162 to one another. Sidewall 163 has inner surface 164 comprising a portion of second surface 132 of the film and outer surface 167 comprising a portion of first surface 131 of the film.

In describing debossed and perforated materials of the present invention, it is useful to refer to certain dimensions of the formed material. Exemplary formed film 150 has a maximum thickness T separating first surface 131 and second surface 132 of the film. Sidewall 163 of each protuberance 155 has an average depth L from the plane of the upper surface of land area 160, measured about the periphery of second aperture 162 in a direction perpendicular said plane. First aperture 161 of protuberance 155 is often an irregular shape. The size of first aperture 161 can be described as having a cross-sectional area such that a circle of diameter D can be inscribed therein. As used herein, an inscribed circle is one that is wholly within first aperture 161 and contacts the edges of aperture 161 at a minimum of two points, such that for every diameter bisecting the circle, there is at least one such contact point in each semicircle, or the diameter connects two such contact points.

Debossed and perforated materials of the present invention comprise protuberances having a ratio of L/T of at least about 5, more preferably a ratio of L/T of at least about 10, more preferably still a ratio of L/T of at least about 15. Debossed and perforated materials of the present invention have a ratio of L/D of at least about 0.5, preferably a ratio of L/D of at least about 0.7, more preferably a ratio of L/D of at least about 1.0. Because debossed and perforated materials of the present invention can have protuberances having an extremely wide variety of shapes, it is possible for such protuberances to have first apertures having more than one inscribed circle. For such irregular-shaped protuberances, the ratio of L/D refers to the portion of the protuberance surrounding a particular inscribed circle of diameter D.

An attribute of the high-pressure liquid film-forming process of the present invention is the ability to retain certain physical properties of a substantially planar flat film in a formed film produced therefrom. Desired physical properties of the substantially planar starting film can generally be substantially retained in the land areas between the protuberances of such formed film, and to some extent in the sidewalls of the protuberances. Due to the physical distortion of the film in the protuberances, the film in the protuberances, especially adjacent the second aperture, generally acquires some differing physical properties from the film in the land area.

A major advantage of processes of the present invention over the prior art vacuum forming processes is the ability to retain surface appearance and properties engineered into a substantially planar film. For example, a substantially planar thermoplastic film having a surface roughness, such as a matte surface or a fine embossed pattern can be debossed and perforated by processes of the present invention while retaining the matte surface or fine embossed pattern on the land area of the formed film, and also to a large extent on the sidewalls of the protuberances of the formed film. This is a particular advantage in achieving debossed and perforated films without a shiny "plastic" look. Such a surface roughness may be present on only one surface of the flat film before forming, as is often the case for a matte finish, or may extend clear through the substantially flat film, as is generally the case for a fine embossed pattern. For films which are transparent or translucent, a surface roughness on either surface of the film is effective in reducing the shiny plastic look on both surfaces.

When such a surface roughness is present on at least one surface of the unformed film, a formed film produced therefrom by processes of the present invention can exhibit a surface roughness on at least one surface of the land area of the formed film, e.g., on either the upper or lower surface of land area 160 of exemplary formed film 150 of FIG. 11. In such case, formed film 150 would also exhibit such surface roughness on at least one surface of sidewall 163 of each perforated protuberance 155 to an average depth of at least about L/4 from the plane of the upper surface of land area 160. However, formed film 150 exhibits a surface smoothness on both inner surface 164 and outer surface 167 of sidewall 163 adjacent second aperture 162 due to the extreme stretching of the film in this region when second aperture 162 is formed during the forming process. Preferred formed films of the present invention exhibit surface roughness on at least one surface of sidewall 163 of perforated protuberance 155 to a depth of at least about L/2 from the plane of the upper surface of land area 160. The depth of such surface roughness on the surface of the sidewalls of the perforated protuberances depends on the properties of the film being formed and the conditions under which it is formed.

FIG. 10 shows exemplary forming screen 127 having surface aberrations 156 on land area 151. A method for producing such a forming screen is disclosed in commonly assigned European Patent Application No. 0,059,506 A2 of Ahr, Mullane, Louis & Ouellette, published Sept. 8, 1982, the disclosure of which is hereby incorporated herein by reference. Another method for producing forming screens having surface aberrations on the forming surface is disclosed in commonly assigned U.S. Pat. No. 4,327,730 issued to Sorensen on May 4, 1982, the disclosure of which is hereby incorporated herein by reference. Sorensen achieves a forming screen having random surface aberrations on both the land areas of the forming surface and on the sidewalls of the depressions in the forming surface, while Ahr, Mullane, Louis & Ouellette discloses a forming screen having a regular pattern of surface aberrations only on the land area of the forming surface. Either type of forming screen can be used in process of the present invention to produce formed materials of the present invention. However, it is preferred to use forming screens having surface aberrations, either random or regular pattern, only on the land area of the forming surface (such as surface aberrations 156 on land area 151 of forming surface 129 of forming screen 127 in FIG. 10).

It has been found that the use of a forming screen having surface aberrations on the land area results in a formed film which conforms more closely to the image of the forming surface of the forming screen than with a forming screen without such surface aberrations is used. Although the present invention is not dependent on any particular mechanism by which this occurs, it is believed to be due primarily to frictional forces between web of film 10 and forming surface 29.

The use of such a preferred forming screen having surface aberrations on the land areas, but not on the sidewalls of the depressions, results in a formed film having a roughness imparted by the forming screen to the land areas of the formed film, but not to the sidewalls of the protuberances of the formed film. When the flat film to be formed has a surface roughness on only one surface of the film and a surface smoothness on the other surface of the film, the resulting formed film exhibits a surface roughness of the land area which would be a combination of the surface roughness of the starting film and a roughness imparted by the surface aberrations of the land area of the forming surface. The formed film also exhibits a surface roughness on at least a portion of one surface of the sidewalls of the protuberances corresponding to the surface roughness on one surface of the starting film, but the formed film exhibits a surface smoothness on the entire other surface of the sidewalls of the protuberances corresponding to the smooth surface of the starting film.

A surface roughness on the first surface (the surface proximate the forming surface of the forming screen) of the flat film to be formed has a similar effect as the surface aberrations on the land area of the forming surface. Such a rough first surface of the film results in a formed film which conforms more closely to the image of the forming surface of the forming screen than when the first surface of the film is smooth. This is also believed to be due primarily to frictional forces between web of film 10 and forming surface 29.

Figure 6:
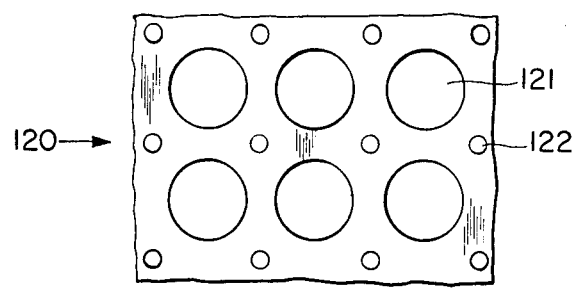
FIG. 6 is a fragmentary plan view of an exemplary debossed and perforated material of the present invention.

Webs of debossed and perforated thermoplastic film having intricate patterns, including perforations having a wide variety of sizes and shapes, can be produced by the high-pressure liquid stream forming processes of the present invention. A fragmentary plan view of an exemplary formed material 120 having large holes 121 and small holes 122 adjacent one another is shown in FIG. 6. Such debossed and perforated materials of the present invention comprise a polymeric film and have adjacent protuberances having D's which differ by a factor of at least about 2, 5, 10, 20, 50 or more.

Formation of such materials is possible using the processes of the present invention because the pressure differential across the thickness of the material being formed is virtually independent of the formation of adjacent areas of the material. This differs from the prior art vacuum forming processes where once a hole is formed in the film, the pressure differential across the thickness of the film in the immediately surrounding area is substantially reduced. Thus it is not usually possible to form very small holes adjacent large ones when using the prior art vacuum forming processes.

Figure 12:
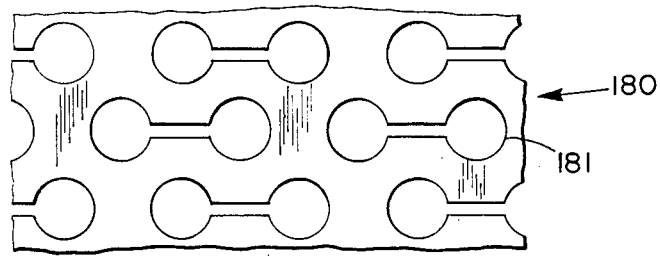
FIG. 12 is a fragmentary plan view of an exemplary debossed and perforated material of the present invention.

This independence of formation to immediately surrounding areas of the material being formed allows processes of the present invention to be used to impart protuberances of a wide variety of shapes to the material being formed. The shapes that can be formed are of an almost infinite variety. For example, shapes having large open areas adjacent narrow open areas can be formed. A fragmentary plan view of an exemplary formed film 180 having irregular shaped holes 181 having adjacent large and narrow open areas is shown in FIG. 12. Such a film has protuberances with a first aperture which has an irregular-shaped cross-sectional area such that at least two circles of diameters D can be inscribed therein such that the two circles do not overlap, and such that the two circles have D's which differ by a factor of at least about 2, 5, 10, 20, 50, or more.

This lack of sensitivity to the size of the opening in the forming screen allows for more flexibility in structures that can be used to support forming screen 27 for the processes of the present invention. For example, if forming structure 28 is used to produce webs of debossed and perforated film in the prior art vacuum forming processes, formation of perforated protuberances has been found to not be complete where holes in forming surface 29 are partially blocked by the metal cell walls of honeycomb 26. Such partial obstruction of the holes in forming surface 29 generally results in an unperforated protuberance using these prior art processes. On the other hand, such partially blocked holes in forming surface 29 generally have little or no effect on the formation of perforated probuberances when the high-pressure liquid stream forming processes of the present invention are used, as long as such blockage does not directly support a portion of the film being formed.

In the prior art processes for producing formed film by vacuum forming of a web of molten film, the film must be cooled below its melt temperature range to set the new bulk conformation of the formed film prior to removing it from the forming surface. The heat transfer required to set the film is often a rate limiting step in such processes. Because the processes of the present invention are performed with the web of film in a solid state throughout the process, no cooling is required to set the film prior to removing it from the forming surface. This allows the processes of the present invention to be run at very high speed, thus providing substantial economic benefits. While the exemplary process shown in FIGS. 1 and 2 can be run at lower speeds, it is typically run at speeds of 2 m/sec or faster. Preferable speeds for such a process are from about 4 m/sec to about 8 m/sec; speeds up to about 15 m/sec or faster are attainable.

While prior art processes where a molten film is fed directly from a film extruder onto a forming surface can achieve moderately high forming rates (up to about 2.5 m/sec is currently achieved on a commercial scale), high molecular orientations are imparted to such formed films produced at such moderately high speeds. Such high molecular orientations are typically unwanted since they induce large anisotropic properties to the formed film. The processes of the present invention can produce formed film at very high speeds without imparting such unwanted molecular orientations in the film since the films are retained at temperatures below their melt temperature range and are not stretched to a large degree.

Figure 7:
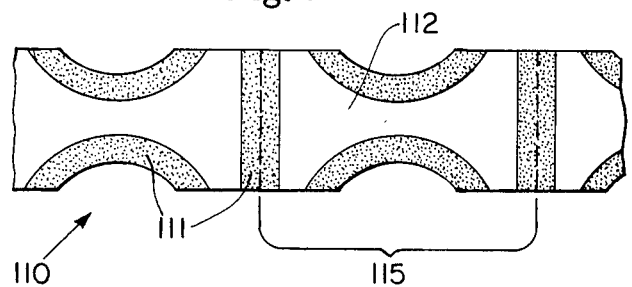
FIG. 7 is a fragmentary plan view of a web of partially formed material of the present invention.

Because there is no molten film that must be solidified, the processes of the present invention can also be run at very high speed where it is desired to form only part of a web of substantially planar material. FIG. 7 shows a portion of a web of thermoplastic film 110 which may be divided into sections 115 for use as cover plies for shaped disposable diapers. Web of formed film 110 is debossed and perforated only in areas 111 which will be the legbands and waistbands of the diaper. Perforated areas 111 will thus provide an air-breathable fit around the legs and waist of the diaper wearer to provide comfort. The remaining area 112 of web of film 110 remains a moisture barrier.

To produce web of film 110 using prior art vacuum film forming processes, the entire web of film (or at least substantial portions of web 110) would normally be molten while areas 111 are debossed and perforated. Then the molten portions of web of film 110 would have to be cooled in order to solidify the film. Rapid cooling of unperforated area 112 would be particularly difficult since there are no perforations in area 112 through which cooling fluid can flow.

Areas 111 of web of film 110 can easily be debossed and perforated while the web of film is in the solid state by the processes of the present invention. The apparatus shown in FIGS. 2 and 3 could be used by providing forming screen 27 with holes in forming surface 29 only in certain spaced areas to provide formed areas 111 on web of film 110. Such a process could easily be performed at high speed since there is no need to solidify the film after forming.

Figure 5:
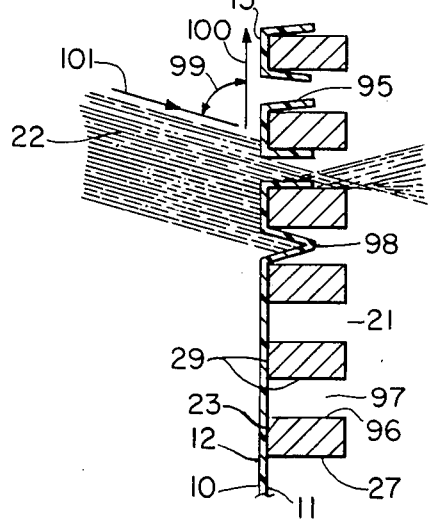
FIG. 5 is an enlarged view of Area 4 of FIG. 3 with the liquid stream impinging the forming surface at an acute angle with the direction of travel of the forming surface.

In producing debossed and perforated webs of material using the processes of the present invention, it was found that the use of forming screens with depressions and holes that were symmetrical with regard to their leading and trailing edges did not always produce webs of formed film with symmetrical debossed protuberances. It was found that the angle at which liquid stream 22 strikes second surface 12 of web of film 10 can affect the symmetry of such protuberances of web of formed film 15. The mechanism that is believed to be occurring is illustrated in FIGS. 4 and 5, where the apparatus and process are viewed perpendicular to forming surface 29. In FIG. 4, liquid stream 22 is set at direction of travel 101 such that it impinges second surface 12 of web of film 10 at an angle about perpendicular to direction of movement 100 of forming surface 29. As a depression 97 approaches liquid stream 22, the portion of web of film 10 at the leading edge of depression 97 is contacted by liquid stream 22 first. This causes the portion of web of film 10 that is stretched into depression 97 to be stretched and ultimately perforated in an unsymmetrical manner, as shown in FIG. 4. It has been found that by setting liquid stream 22 with direction of travel 101 at the proper angle 99 to direction of movement 100 of forming surface 29, substantially symmetrical perforated protuberances can be achieved. Angle 99 is defined herein as, when viewed perpendicular to forming surface 29, the angle between direction of travel 101 of liquid stream 22 as it approaches forming surface 29 and direction of movement 100 of forming surface 29 from the point where liquid stream 22 impinges forming surface 29. Angle 99 is preferably an acute angle. The proper angle 99 for setting liquid stream 22 will depend on the pattern of forming surface 29 of forming screen 27 and the speed at which web of film 10 passes by liquid stream 22. At very high speeds, the desired angle 99 of liquid stream 22 approaches an angle perpendicular to the direction of travel of forming surface 29.

Figure 9:
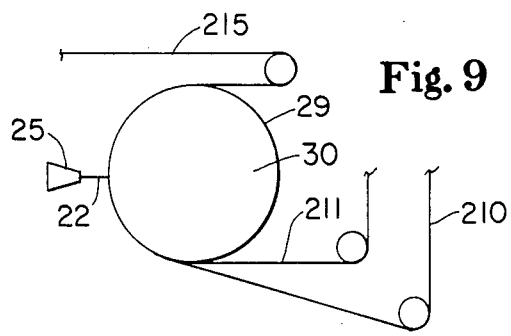
FIG. 9 is a fragmentary schematic flow diagram of a process of the present invention for producing laminates of formed material.

The processes of the present invention are particularly useful for producing debossed and perforated laminates of thermoplastic film and other materials such as metal foils, nonwoven materials, and paper. Processes of the present invention can be used not only to deboss and perforate such laminates but also to cause the plies of the laminate to be adhered together. This can be done using the exemplary process shown in FIGS. 1 and 2 by feeding two (or more) webs of substantially planar materials simultaneously over forming drum 30. A portion of such a process is shown in FIG. 9 where web of thermoplastic film 210 and web of metal foil 211 are fed in planar contacting relationship onto forming surface 29 of forming drum 30 and are formed by liquid stream 22 from spraying system 25 to produce debossed and perforated laminate 215. The third dimensional perforated protuberances of formed laminate 215 provide an intermeshing of the thermoplastic film and metal foil layers such that the plies of the laminate are held together.

Figure 8:
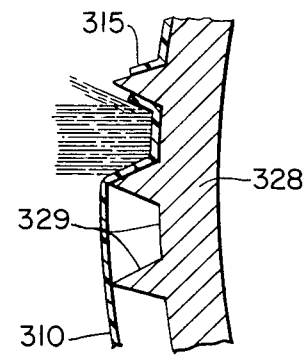
FIG. 8 is a simplified schematic cut-away end view of a portion of another apparatus for forming a web of material.

The illustrations provided hereinbefore have described film formation on female forming surfaces where the material being formed is forced by a high pressure liquid stream into depressions or concavities of the forming surfaces. Such female forming surfaces are primarily suited for material having greater compressive strength then tensile strength. For forming materials having greater tensile strength than compressive strength, male forming surfaces such as that illustrated in FIG. 8 are preferred. Web of deformable material 310 is formed on male forming surface 329 of forming structure 328 due to the action of impinging liquid stream 322, thus producing web of formed material 315.

EXAMPLES

The following examples are presented as illustrations of the present invention; they are not intended to limit the scope of the invention in any way.

EXAMPLE 1

A web of debossed and perforated film was made substantially by the process depicted in FIGS. 1, 2 and 3 and disclosed hereinbefore. Forming screen 127 of FIG. 10 was used to form the film. Web of film 10 was a 0.025 mm thick and 19.4 cm wide web of low density polyethylene film available commercially from Consolidated Thermoplastics Company, Harrington, Del., as product No. 23932. Web of film 10 had a matte finish on surface 11 and was corona discharge treated on surface 12.

Forming drum 30 was driven such that the speed of web of film 10 was about 4 m/sec. Driven S-wrap rolls 31/32, 33/34, and 35/36 were driven at different surface speeds to ensure that there was adequate tension on web of film 10 and web of formed film 15 throughout the process. These surface speeds of driven S-wrap rolls 31/32, 33/34, and 35/36 as a percentage of the speed of forming drum 30 were 97.5%, 108%, and 113%, respectively. The tension measured by tension measuring rolls 58, 67, and 82 was about 0.9 kg, 0.5 kg, and 1.2 kg, respectively during the run.

Web of film 10 was debossed and perforated by the flow of liquid stream 22 from five spray nozzles 90 evenly spaced 4.8 cm apart and centered across web of film 10. Nozzles 90 were wash jets, type 2540, available commercially from Spraying Systems Co., Wheaton, Ill.; they provide a flat spray at an angle of 25°. Liquid stream 22 was water supplied to nozzles 90 at a temperature of 70° C. at a pressure of 830 N/cm² (1200 psig), resulting in a flow of 5.7 l/sec. of water through the five nozzles. The nozzles were set such that the spray angle of 25° was parallel to and centered in the cross-machine direction. (The thinnest dimension of the spray was parallel to the machine direction—the direction of travel of forming surface 29.) The nozzles were set such that the flat spray of water stream 22 impinged surface 12 of web of film 10 at an angle of 81° to the direction of travel of forming surface 29.

Web of formed film 15 thus produced retained the matte finish on surface 11 in the land areas and in a substantial portion of the protuberances of formed film 15. The corona discharge ionization was retained on a substantial portion of surface 12 of web of formed film 15.

Web of formed film 15 thus produced had perforated protuberances having an average depth L of about 0.65 mm and an average inscribed circle diameter D of about 0.8 mm. Thus web of formed film 15 had a ratio of L/T of about 25 and a ratio of L/D of about 0.8. The dimensions L and D were determined by optical measurements using moderate magnification.

EXAMPLE 2

A web of debossed and perforated film was made according to the process used in Example 1 except for the following: forming drum 30 was driven such that the speed of web of film 10 was about 7.5 m/sec; water was fed to nozzles 90 at a pressure of 1040 N/cm² (1500 psig) with a resulting flow of 7.6 l/sec of water through the five nozzles; the nozzles were set such that the flat spray of water stream 22 impinged surface 12 of web of film 10 at an angle of 85° to the direction of travel of forming surface 29.

The web of formed film thus produced had substantially the same characteristics as the web of formed film produced by Example 1.

EXAMPLE 3

A web of debossed and perforated film was made by the process of Example 1 except that web of film 10 was a high tear strength polypropylene blend commercially available from Exxon Chemical Company, Houston, Tex., as product no. XELF 4251.

The web of formed film thus produced had perforated protuberances having an average depth L of about 0.53 mm and an inscribed circle diameter of about 0.8 mm. Thus the web of formed film had a ratio of L/T of about 21 and a ratio of L/D of about 0.7.

While particular embodiments of the invention have been illustrated and described, it would be obvious to those skilled in the art that various changes and modifications can be made without departing from the spirit and scope of the invention. It is intended to cover, in the appended claims, all such modifications that are within the scope of this invention.

What is claimed is:

1. A process for permanently transforming a substantially continuous web of substantially planar, deformable material comprising a film having an indefinite length, a first surface and a second surface into a web of formed material having a substantial third dimensional structure perpendicular to the plane of said material without substantially altering the physical properties or the thermo-mechanical history of said substantially planar web, said material having a transformation temperature range, said process comprising the steps of:

(a) providing said web of material on a forming structure with said first surface of said web of material proximate a forming surface of said forming stucture, said forming surface exhibiting a three-dimensional profile, said forming surface moving in a direction of said length of said web of material and carrying said web of material in said direction;

(b) applying a substantially unconstrained liquid stream which is substantially stationary in the direction of travel of said moving web substantially uniformly to said second surface of said moving web of deformable material in those areas to be transformed, said substantially unconstrained liquid stream having sufficient force and mass flux to cause said moving web of material to be deformed toward said forming surface upon contact therebetween, such that said material acquires a substantial, permanent three-dimensional conformation in the image of said forming surface of said forming structure before passing beyond the influence of said substantially stationary liquid stream; and (c) controlling the temperature of said web of material such that it remains below said transformation temperature range of said material throughout said process, thereby maintaining said web of substantially planar material in a substantially solid state throughout said process.

2. The process of claim 1 wherein said material comprises a thermoplastic film having a melt temperature range, and said transformation temperature range is said melt temperature range of said film.

3. The process of claim 2 wherein surface appearance and mechanical properties of said film prior to forming are substantially retained in said formed film.

4. The process of claim 1 wherein said liquid stream is applied to said second surface of said web of material from high pressure spray nozzles, liquid being supplied to said spray nozzles at a pressure of at least about 350 N/cm$^2$ (500 psig).

5. The process of claim 3 wherein said liquid stream is applied to said second surface of said web of material from high pressure spray nozzles, liquid being supplied to said spray nozzles at a pressure of at least about 700 N/cm$^2$ (1000 psig).

6. The process of claim 4 wherein said liquid is water at a temperature of from about 40° C. to about 90° C.

7. The process of claim 6 wherein said forming surface is the cylindrical surface of a forming drum.

8. The process of claim 6 wherein said forming surface is the outer surface of an endless belt.

9. A process for permanently transforming a substantially continuous web of substantially planar, deformable material comprising a film into a web of debossed and perforated material without substantially altering the physical properties or the thermo-mechanical history of said substantially planar web, using a forming structure having a three-dimensionally patterned forming surface and an opposed surface, said forming surface comprising depressions which have sidewalls and end in holes, said forming structure being open from said holes in said forming surface to said opposed surface, said web of material having an indefinite length, a first surface and a second surface, said material having a transformation temperature range, said process comprising the steps of:

(a) providing said web of material on said forming surface with said first surface of said web of material proximate said three-dimensionally patterned forming surface of said forming structure, said forming surface moving in a direction of said length of said web of material and carrying said web of material in said direction;

(b) applying a substantially unconstrained liquid stream which is substantially stationary in the direction of travel of said moving web substantially uniformly to said second surface of said web of deformable material in those areas to be transformed, said substantially unconstrained liquid stream having sufficient force and mass flux to cause perforations to be created in said web of material in the areas coinciding with said depressions in said forming surface immediately upon contact therebetween;

(c) flowing at least a portion of said substantially stationary liquid stream through said perforations in said web of material, through said holes in said forming surface, and through said forming structure so long as said moving web remains subject to said substantially stationary liquid stream; and (d) controlling the temperature of said web of material such that said material remains below said transformation temperature range throughout said process, thereby maintaining said web of substantially planar material in a substantially solid state throughout said process;

said liquid stream having sufficient force and mass flux to cause said web of material to be extended into said depression and to cause said first surface of said web of material to be urged toward said sidewalls of said depressions, such that perforated protuberances are formed in said web of material.

10. The process of claim 9 wherein said material comprises a thermoplastic film having a melt temperature range, and said transformation temperature range is said melt temperature range of said film.

11. The process of claim 10 wherein said liquid stream is applied to said second surface of said web of material from high pressure spray nozzles, liquid being supplied to said spray nozzles at a pressure of at least about 350 N/cm$^2$ (500 psig).

12. The process of claim 10 wherein said liquid stream is applied to said second surface of said web of material from high pressure spray nozzles, liquid being supplied to said spray nozzles at a pressure of at least about 700 N/cm$^2$ (1000 psig).

13. The process of claim 11 wherein said thermoplastic film is selected from the group consisting of polyethylenes, polypropylenes and copolymers and blends containing these materials.

14. The process of claim 13 wherein said film has a thickness of from about 0.01 mm to about 0.04 mm.

15. The process of claim 11 wherein said liquid is water at a temperature of from about 40° C. to about 90° C.

16. The process of claim 15 wherein a vacuum is applied beneath said opposed surface of said forming structure in an area where said liquid stream flows through said holes into said forming structure.

17. The process of claim 11 wherein, when viewed perpendicular to said direction of movement of said forming surface, said liquid stream is set at a direction of travel and impinges said forming surface at a point such that an angle between said direction of travel of said liquid stream as it approaches said forming surface and said direction of movement of said forming surface from said point where said liquid stream impinges said forming surface is an acute angle.

18. The process of claim 10 wherein said forming surface moves in said direction of said length of said web of material at a linear speed of about 4 m/sec or faster.

19. The process of claim 18 wherein only a portion of said web of material is formed.

20. The process of claim 10 wherein surface appearance and mechanical properties of said film prior to forming are substantially retained in said debossed and perforated web of material.

21. The process of claim 10 wherein each said protuberance of said web of debossed and perforated material comprises a sidewall having an inner surface comprising a portion of said second surface of said film and an outer surface comprising a portion of said first surface of said film, said film exhibiting a surface roughness on at least one of said first and second surfaces of said film prior to forming, and said film exhibiting said surface roughness on a portion of at least one of said inner and outer surfaces of said sidewall of each said protuberance of said debossed and perforated film.

22. The process of claim 11 wherein said first surface of said substantially planar material has a surface roughness.

23. The process of claim 11 wherein said forming surface comprises land areas between said depressions, said land areas comprising a surface roughness.

24. An apparatus for permanently transforming a substantially continuous web of substantially planar material comprising a film having an indefinite length into a formed material having a substantial third dimensional structure perpendicular to the plane of said material without substantially altering the physical properties or the thermo-mechanical history of said substantially planar web, said material having a transformation temperature range, said apparatus comprising:

a forming structure having a three-dimensionally patterned forming surface;

(b) means for moving said forming surface in a direction of said length of said web of material;

(c) means for applying a substantially unconstrained liquid stream to said forming surface with sufficient force and mass flux to cause said web of material to be formed substantially in the image of said three-dimensionally patterned forming surface; and (d) means for controlling the temperature of said web of material such that the temperature of said material remains below said transformation temperature range.

25. The apparatus of claim 24 wherein said means for applying said liquid stream comprises high-pressure spray nozzles.

26. The apparatus of claim 25 wherein said nozzles provide said liquid stream in a flat, fan-shaped spray having a fan angle of no more than about 30° in the cross-machine direction.

27. The apparatus of claim 25 wherein said nozzles are set such that, when viewed perpendicular to said direction of movement of said forming surface, said liquid stream has a direction of travel, and the angle between said direction of travel of said liquid stream and said direction of movement of said forming surface is an acute angle.

28. The apparatus of claim 24 wherein said means for controlling temperature of said web of material comprises means for controlling temperature of said liquid stream.

29. An apparatus for permanently transforming a substantially continuous web of substantially planar material comprising a film having an indefinite length into a debossed and perforated material, said material having a transformation temperature range, said apparatus comprising:

(a) a forming structure having a patterned forming surface and an opposed surface, said forming surface comprising depressions which have sidewalls and end in holes, said forming structure being open from said holes in said forming surface to said opposed surface;

(b) means for moving said forming surface in a direction of said length of said web of material;

(c) means for applying a liquid stream to said forming surface with sufficient force and mass flux to cause said web of material to be formed substantially in the image of said forming surface and to cause perforated protuberances to be formed in said web of material; and (d) means for controlling the temperature of said web of material such that the temperature of said material remains below said transformation temperature range.

30. The apparatus of claim 29 wherein said forming surface comprises land areas between said depressions, said land areas comprising a surface roughness.

31. The apparatus of claim 30 wherein said means for applying said liquid stream comprises high-pressure spray nozzles which provide said liquid stream in a flat, fan-shaped spray having a fan angle of no more than about 30° in the cross-machine direction.

32. The apparatus of claim 30 wherein said means for applying said liquid stream comprises high-pressure nozzles, said nozzles being set such that, when viewed perpendicular to said direction of movement of said forming surface, said liquid stream has a direction of travel, and the angle between said direction of travel of said liquid stream and said direction of movement of said forming surface is an acute angle.

33. The apparatus of claim 29 wherein said means for controlling temperature of said web of material comprises means for controlling temperature of said liquid stream.

* * * * *

UNITED STATES PATENT AND TRADEMARK OFFICE
CERTIFICATE OF CORRECTION

PATENT NO. : 4,695,422
DATED : September 22, 1987
INVENTOR(S) : John J. Curro, Alan J. Trusty, George M. Vernon It is certified that error appears in the above-identified patent and that said Letters Patent is hereby corrected as shown below:

Column 1, line 9, "process" should read -- processes --.

Column 2, line 65, after "cooling", insert -- of --.

Column 3, line 24, "web" should read -- webs --.

Column 5, line 19, "device" should read -- devices --.

Column 6, lines 5-6, "temperature" should read -- temperatures --.

Column 6, line 47, delete "of".

Column 8, line 30, "spary" should read -- spray --.

Column 9, line 43, "(non-preforated)" should read -- (non-perforated) --.

Column 10, line 61, "The" starts a new paragraph.

Column 11, line 42, after "surface" insert -- , --.

Column 11, line 43, "subsequent" should read -- Subsequent --.

Column 12, lines 32-33, "anytemperature" should read -- any temperature -

UNITED STATES PATENT AND TRADEMARK OFFICE
CERTIFICATE OF CORRECTION

PATENT NO. : 4,695,422

DATED : September 22, 1987

INVENTOR(S) : John J. Curro, Alan J. Trusty, George M. Vernon

It is certified that error appears in the above-identified patent and that said Letters Patent is hereby corrected as shown below:

Column 16, line 6, "with" should read -- when --.

Column 17, line 26, "probuberances" should read -- protuberances --.

Column 18, line 4, "air-breathable" should read -- air-breatheable --.

Column 19, line 22, "then" should read -- than --.

Column 19, line 48, "different" should read -- differential --.

Column 23, line 36, before "a forming structure" insert -- (a) --.

Signed and Sealed this

Eighth Day of March, 1988

*Attest:*

DONALD J. QUIGG

*Attesting Officer*     *Commissioner of Patents and Trademarks*